United States Patent [19]

Bacso

[11] 3,978,048

[45] *Aug. 31, 1976

[54] 17α-SUBSTITUTED-ALLENE-BEARING STEROIDS

[75] Inventor: Imre Bacso, Morristown, N.J.

[73] Assignee: Sandoz, Inc., E. Hanover, N.J.

[ * ] Notice: The portion of the term of this patent subsequent to June 10, 1992, has been disclaimed.

[22] Filed: Feb. 25, 1975

[21] Appl. No.: 552,956

Related U.S. Application Data

[60] Division of Ser. No. 379,160, July 13, 1973, Pat. No. 3,888,849, which is a continuation-in-part of Ser. No. 219,555, Dec. 1, 1972, abandoned.

[52] U.S. Cl. .................. 260/239.55 R; 260/239.5; 260/397.4; 260/397.45; 260/397.5; 424/243
[51] Int. Cl.² ........................................ C07D 471/00
[58] Field of Search .................. 260/397.45, 239.55

[56] References Cited

UNITED STATES PATENTS 3,888,849    6/1975    Bacso ........................... 260/397.45

*Primary Examiner*—Elbert L. Roberts
*Attorney, Agent, or Firm*—Gerald D. Sharkin; Richard E. Vila; Frederick H. Weinfeldt

[57] ABSTRACT

Steroidal compounds of the invention bear a 17β-oxygenated group and a 17α-Ψ-alkyl substituted allene group, e.g., 17α-(penta-1′-2′-dienyl)-estra-4,9-dien-17β-ol-3-one, and are prepared by a procedure, e.g., involving reacting a corresponding intermediate bearing a 17α-(3′-dialkylamino-3′-alkyl-substituted-1′-propynyl)-group with a complex hydride. The steroidal compounds are useful as pharmaceuticals, e.g., as progestational agents.

44 Claims, No Drawings

17α-SUBSTITUTED-ALLENE-BEARING STEROIDS

This is a division of application Ser. No. 379,160 filed July 13, 1973 (now U.S. Pat. No. 3,888,849) which in turn is a continuation-in-part of then copending application Ser. No. 219,555, filed Jan. 20, 1972 (now abandoned).

This invention relates to steroidal compounds, and more particularly, to steroidal compounds bearing at the 17α-position a 3-alkyl-substituted allene-function, to the preparation of such compounds and to intermediates in said preparation, as well as to therapeutic compositions containing said compounds and the use of such compounds.

The steroidal compounds of this invention are conveniently represented by Formula I:

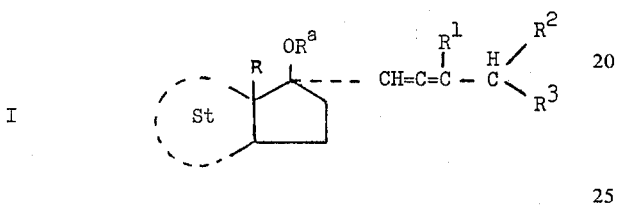

wherein
St is a gonene residue;
R is alkyl having from 1 to 4 carbon atoms;
$R^a$ is a hydrogen atom, or the residue of a hydrolyzable ester or ether;
$R^1$ is a hydrogen atom or alkyl having from 1 to 6 carbon atoms;
$R^2$ is a hydrogen atom or alkyl having from 1 to 8 carbon atoms, preferably from 1 to 6 carbon atoms;
$R^3$ is a hydrogen atom, alkyl having from 1 to 8 carbon atoms, preferably from 1 to 6 carbon atoms, or aryl; or
$R^1$ and $R^3$ may be joined so as to form a polymethylene bridge having from 1 to 12 carbon atoms, preferably from 3 to 5 carbon atoms.

The term alkyl above, includes from example, methyl, ethyl, propyl, butyl, amyl, hexyl, heptyl and octyl, including isomers where they exist, but are preferably unbranched. The term aryl is intended to include phenyl and phenyl having one or two substituents, independently, from the group of fluoro and alkyl having from 1 to 6 carbon atoms. By the term polymethylene bridge is intended part of the structure

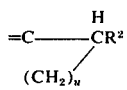

wherein $u$ is an integer of from 3 to 12, thus providing cycloalkyl rings having from 5 to 14 ring carbon atoms.

The term hydrolyzable ester is intended to include those ester functions which may be hydrolyzed under aqueous basic conditions, such as lower alkanoyls, having for example from 2 to 4 carbon atoms, e.g. acetyl, propionyl and butyryl, and acetoacetyl.

The term hydrolyzable ether in $R^a$ and $R^8$ is intended to include those ether functions which may be readily hydrolyzed under aqueous acid conditions, e.g. tetrahydropyran-2-yloxy, tetrahydrofuran-2-yloxy and 4-methoxytetrahydropyran-4-yloxy.

The term gonene residue is intended to include steroidal residues of the estrene and androstene skeletons which include the following partial structures:

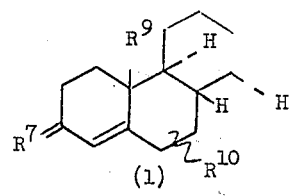

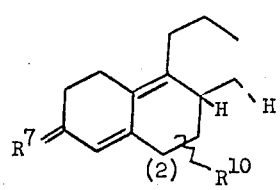

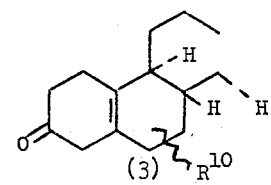

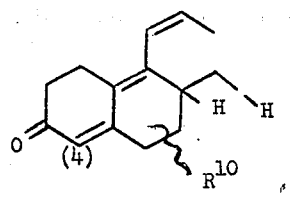

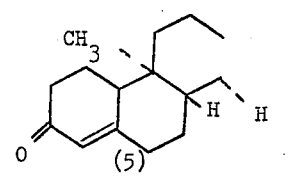

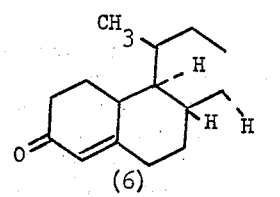

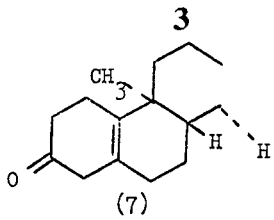

(7)

and

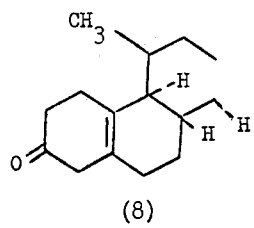

(8)

wherein
R⁷ is oxo, or

or

R⁸ is a hydrogen atom, a hydrolyzable ether or ester residue, as described above;
R⁹ is a hydrogen atom or methyl; and
R¹⁰ is a hydrogen atom, 6α-methyl or 7α-methyl.

A class of compounds of Formula I where R" = a hydrogen atom, i.e. Compounds Ia, are obtainable by Process A, i.e. reduction of a corresponding compound of formula II, with a complex metal hydride:

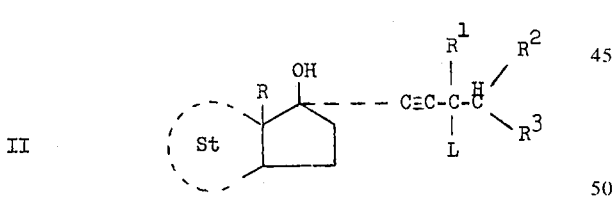

wherein
St, R, R¹, R² and R³ are as above defined, and L is either
L', i.e.

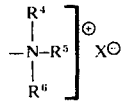

wherein
each of R⁴ and R⁵, independently, represents alkyl having from 1 to 6 carbon atoms;
cycloalkyl having from 5 to 7 ring carbons, e.g. cyclopentyl, cyclohexyl or cycloheptyl; or
R⁴ and R⁵ together with N represents a heterocyclic ring having from 5 to 7 members, having the structure

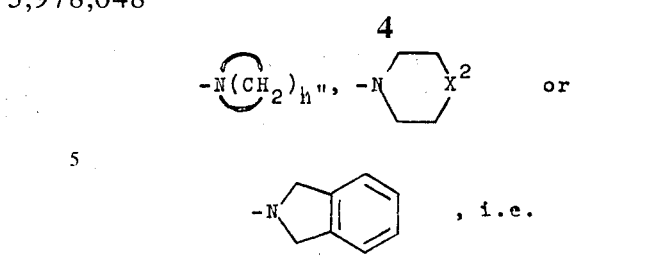

wherein n'' is a whole integer of from 4 to 6; and
X² is oxygen or sulfur, i.e., selected from the group consisting of pyrrolidino, piperidino, homopiperidino, morpholino, thiomorpholino or isoindolino;
R⁶ represents alkyl having from 1 to 6 carbon atoms, and
X is an anion derived from a mineral acid or an organic sulfonic acid, provided that X is not fluoro; or
L is L², i.e., tetrahydrofuran-2-yloxy, tetrahydropyran-2-yloxy, or 4-methoxytetrahydropyran-4-yloxy. The complex metal hydride used in the above-mentioned process A serves as a hydride-ion source and preferably is a hydride of the Formula (IIIa):

IIIa.

wherein
Y is an alkali or alkaline earth metal cation having one unit of valency, such as lithium, sodium, potassium, Ca/2 or Mg/2,
M is aluminum, gallium or boron; and each of Z¹, Z² and Z³ is, independently, a hydrogen atom, alkyl, lower alkoxy or lower alkoxyalkoxy;
or of the Formula (IIIb);

IIIb.

wherein
M is as defined above and each of Z⁴ and Z⁵ is, independently, a hydrogen atom or alkyl,
provided that when M is boron then Z⁴ and Z⁵ are not both hydrogen atoms.

The alkyl and lower alkoxy portions of Compounds IIIa or IIIb have from 1 to 6 carbons, while the alkylene portions of the alkoxyalkoxy moieties thereof have from 2 to 6 carbon atoms and they include the isomeric forms where they exist, but are preferably unbranched. Representative of complex metal hydrides are lithium aluminum hydride, lithium borohydride, sodium dihydro bis-(2-methoxyethoxy) aluminate, lithium gallium hydride, magnesium aluminum hydride, lithium diisobutylmethyl aluminum hydride, lithium trimethoxy aluminum hydride, diethyl aluminum hydride and di-n-butyl borane. Lithium aluminum hydride or sodium dihydro bis-(2-methoxyethoxy) aluminate is preferred.

Process A should be carried out in a medium which is not detrimental to the reaction, such as in an aprotic organic solvent, e.g. an ether such as diethyl ether, tetrahydrofuran or dioxane, or an aromatic medium, such as benzene or toluene or pyridine. A solvent may be used which is capable of dissolving a Compound II where L=L', at the reaction temperature, e.g. pyridine. The medium may be a mixture or a single material. The reaction, e.g. may be carried out at from about −40° to +120° C., e.g. at the boiling point of the medium. However, temperatures of from about −10° to +50° C. are preferred. While the higher temperatures result in a faster reaction rate, reactions carried out at lower temperature tend to give purer products. The reaction product (Compound Ia) may be recovered by conventional means, e.g. by carefully adding a small amount of water or aqueous salt or inorganic base, e.g. sodium sulfate or sodium chloride, to the reaction mixture, filtering off the inorganic by-products or hydrolysis products of the hydride ion source, and then separating the Compound Ia from the organic phase by such means as precipitation, extraction, crystallization, chromatography or liquid-liquid extraction.

It will be appreciated that when the desired Compound Ia bears a 3-oxo or 3-acyl function such group will likely be converted during the reduction or subsequent recovery procedure in which exposure to aqueous basic conditions can occur. Accordingly, a corresponding Compound Ia bearing a 3-hydroxy function is obtained which can be oxidized to oxo or acylated to the desired ester by conventional means. Alternatively, a "protected" form of 3-oxo function may be employed, i.e. a form which is not effected by the reaction condition of process A or the work-up, but can be readily converted to an oxo function by hydrolysis, e.g. a ketal group. As is noted above, the Compounds Ia represent a class of Compounds I wherein $R^a$ is a hydrogen atom. Accordingly, where Compounds I wherein $R^a$ is other than a hydrogen atom are desired, such compounds may be obtained by conventional means. Process A, therefore, yields either Compounds Ia in "protected" form or 3-OH bearing-Compounds Ia, which may be converted by conventional means to compounds within the scope of Compounds I. Compounds of the structural types (3), (7) and (8), i.e. compounds having a 3-oxo-5(10)-unsaturated system tend to undergo rearrangement under the basic conditions of Process A, and the conventional methods of recovery of the reaction product from the resulting reaction mixture, to their corresponding 3-oxo-4-unsaturated isomers, i.e. to compounds of types 1 (where $R^9$=H), 5 and 6, respectively. Accordingly, wherein optimum yield of a compound of type (3), (7) or (8) is desired, use of protected forms, and subsequent hydrolysis thereof is also preferred.

Compounds II where L=L' used in process A may be obtained by quaternizing (process B) a suitable 17α-N, N-dialkylamino-alkynyl-17β-hydroxy Compound IV of the formula:

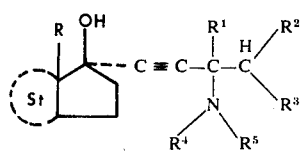   IV wherein St, R, $R^1$, $R^2$, $R^3$, $R^4$ and $R^5$ are as defined above, with a compound the formula V:

$R^6X$   V wherein $R^6$ and X are as defined above.

The quaternization step (process B) may be carried out in the conventional manner for preparing a quaternary ammonium salt from a tertiary amine, e.g. at a temperature of from about −20° to 100° C. A solvent may be used, e.g. acetone or acetonitrile. Where a Compound V is liquid under the reaction conditions, it may be used in excess to serve at the reaction medium. Preferred Compounds V are methyl iodide and methyl p-toluene sulfonate.

Compounds IV, used in process B are obtainable by reaction (process C¹) between a 17α-ethynyl-17β-hydroxy Compound VI;

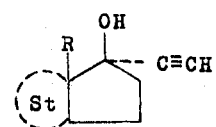   VI wherein St and R are as defined above, and an enamine (VII) of the formula:

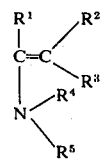   VII wherein $R^1$, $R^2$, $R^3$, $R^4$ and $R^5$ are as defined above.

Process C¹ is conveniently carried out at temperatures of from about 60° to 200° C., preferably from about 80° to 150° C., and in a suitable solvent, e.g. an ether, such as p-dioxane, diglyme or triglyme, and in the presence of free copper or silver or of a salt, adduct or complex thereof or of gold capable of providing monovalent ions under the reaction conditions. As Examples of suitable salts may be given cuprous chloride, cuprous bromide, cuprous nitrate, cuprous acetate, silver or gold (I) chloride or bromide, or silver nitrate. As Examples of complexes may be given copper, silver and gold cyanides. Where any of the reactants is a liquid at the reaction temperature, the solvent may be omitted, and a reactant employed in excess to serve as the reaction medium. Water should be excluded from the reaction, and it is preferable to carry out the reaction in an inert atmosphere, e.g. under dry nitrogen gas.

Where a Compound Ia is desired wherein $R^1$ is a hydrogen atom, (a Compound Ib) then the preparation of a suitable Compound IV may be carried out by process C² which involves reacting a Compound VI with a secondary amine of Formula VIII, and a suitable aldehyde of the Formula IX, i.e.

   VIII wherein R[4] and R[5] are as defined above, and

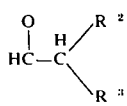   IX wherein R[2] and R[3] are as defined above.

The reaction (Process C[2]), may be conveniently carried out in a suitable solvent, e.g. a cyclic ether such as p-dioxane or tetrahydrofuran, at moderate temperatures, e.g. 10° to 50° C., preferably at 20° to 30° C., and in the presence of monovalent ions of copper, silver or gold, provided by the free metals or the adducts, salts or complexes thereof as described above with respect to process C[1].

Suitable enamine reagents (VII) are known, or where not known may be prepared by procedures analogous to those for preparing the known compounds. For example, by reacting a suitable secondary amine, i.e. a compound VIII as defined above, with a suitable α-hydrogen-containing carbonyl Compound X

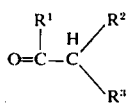   X wherein R[1], R[2] and R[3] are as defined above.

It will be noted that where R[1] is a hydrogen atom, the compound X is an aldehyde and where R[1] is alkyl the compound X is a ketone. The reaction is conveniently carried out in conventional manner, e.g. as described in "Enamines, Synthesis, Structure and Reactions" by A. Gilbert Cook (Marcel Dekker, N.Y. and London, 1969).

Compounds VI are known or where not known may be prepared from known compounds by procedures analogous to those for preparing the known compounds, e.g. by treating with an ethynylating agent a corresponding 17-oxo bearing steroidal compound of the formula XII;

XII   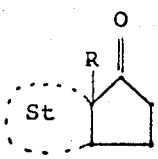

in which St and R are as defined above, protected forms of compounds XII being appropriately employed where St is of a type bearing a 3-oxo function.

The above-described preparations of a Compound Ia by process A) from a Compound II', i.e. a Compound II in which L=L' which in turn is obtainable by process (B) from a Compound IV, which in turn is obtainable from a Compound VI by process (C[1]) is conveniently represented by Reaction Scheme A which follows. The above-described preparation of a Compound Ib is likewise conveniently represented by Reaction Scheme B which also follows. It can be seen that the preparation of a Compound Ib is analogous to the preparation of a Compound Ia, except that the Compounds IV therefor are obtained by process C[2]. In the reaction schemes, St, R, R[1], R[2], R[3], R[4], R[5], R[6] and X are as defined above.

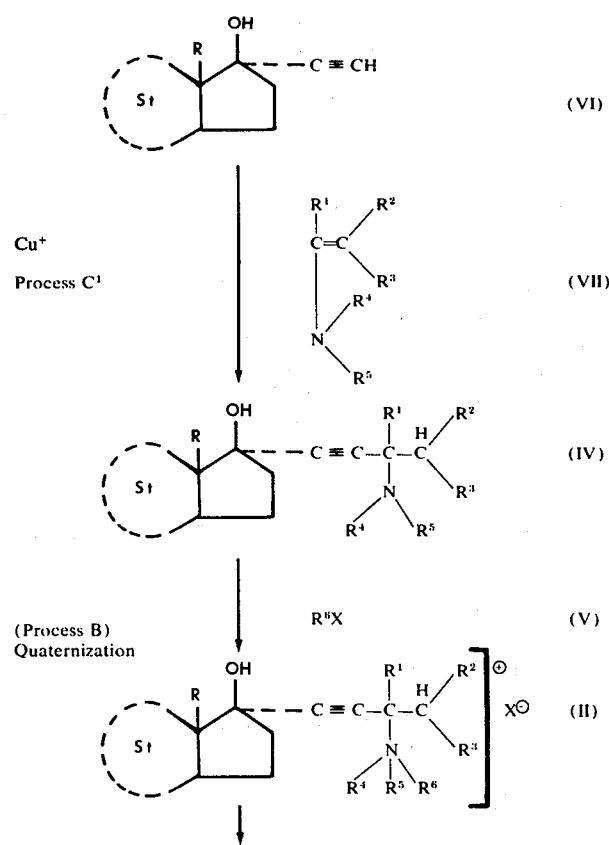

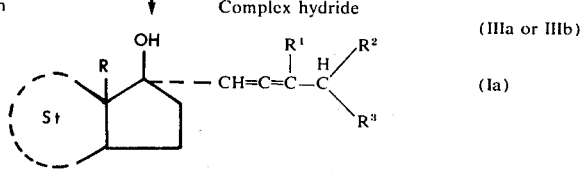

Those compounds of formula IV, above, in which $R^1$ signifies a hydrogen atom or a methyl radical when $R^2$ and $R^3$ both signify hydrogen atoms, are preferably obtained by reacting a compound of formula XII, as defined above, with an organo-metallic reagent of formula XIII,

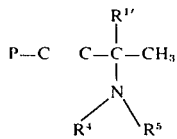

in which $R^4$ and $R^5$ are as defined above,
$R^{1\prime}$ signifies a hydrogen atom or a methyl group, and
P signifies a monovalent active metal or active metal halide radical, e.g. an alkali metal such as lithium, sodium or potassium, Zn/2, Al/3 or -MgBr or -MgI, and hydrolysing the resulting product.

The reaction may be carried out under conditions conventionally employed in carrying out the well-known Grignard-type reactions, e.g. in a non-aqueous organic medium at a temperature of from −30° to 100°C., preferably from −20° to 50°C. followed by standard hydrolysis of the resulting salt, for example, employing water or an aqueous salt or dilute acid or base solution such as a saturated aqueous ammonium chloride or sodium chloride solution.

The reaction medium employed is preferably chosen having regard to the organo-metallic reagent used. Thus, for example, when P signifies -MgBr, -MgI or Li, the medium may be cyclic or acyclic ether, e.g. diethyl ether or tetrahydrofuran, and when P signifies sodium, the medium may, for example, be liquid ammonia/ether, ethylenediamine/tetrahydrofuran, dioxane, pyridine or dioxane/pyridine. Where an organo-metallic reagent is employed which is prepared in situ in ethylenediamine, the ethylenediamine can be used as co-solvent in the reaction.

As any oxo function present on the compound of formula XII, in addition to that at the 17-position, e.g. at the 3-position, may also react with the organo-metallic reagent of formula XIII, such oxo function should be protected, for example, by employing an enol ether or ketal form thereof. A particularly convenient protected form of a compound of formula XII when St is of formula (1) when $R_7$ signifies oxo, or of formula (3), (5), (6), (7) or (8), is the 3-methoxy-2,5(10)-diene form thereof.

In addition, if $R^8$ of a compound of formula XII is a hydrolysable ester residue, then during the hydrolysis stage, such functions might be hydrolysed as basic aqueous conditions are encountered at that stage. Also, in the recovery of a compound of formula I from process (A), such aqueous basic conditions can be encountered, and a hydrolysable ester residue could similarly be hydrolysed. Hence, where a compound of formula I bearing a ester residue at position 3 is desired, such function should preferably not be present on a compound of formula II during process (A), or in the preparation of a compound of formula II, but should preferably be subsequently introduced by employing a convention acylation technique.

Those compounds of formula II², (Compounds II in which L is $L^2$, i.e. a tetrahydrofuran-2-yloxy, tetrahydropyran-2-yloxy or 4-methoxytetrahydropyran-4-yloxy radical) may be obtained by reacting a compound of formula XII, above, with a Grignard reagent formed by treating a compound of formula XIV,

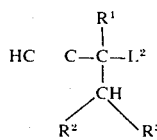

in which $R^1$, $R^2$ and $R^3$ are as defined above, and $L^2$ signifies a tetrahydrofuran-2-yloxy, tetrahydropyran-2-yloxy or 4-methoxytetrahydropyran-4-yloxy radical, with an organo-metallic compound such as butyl lithium or ethyl magnesium bromide.

The preparation of the Grignard reagent and the subsequent reaction thereof with the compound of formula XII may be carried out in conventional manner, e.g. as described above in connection with the reaction of a compound XII with a compound XIII.

As will be appreciated by those skilled in the art, various Compounds I may be interconverted by means of known reactions to compounds corresponding to Compounds I, e.g. by acylation, quinone oxidation of hydroxy groups, hydrolysis of ketals or enol ethers, reduction of ketones or etherification. Such conversions may be employed to advantage when particular substituents would be susceptible to undesired modification. Similarly, intermediates for the preparation of Compounds I, may be interconverted by employing conventional procedures or by selection of appropriate starting materials to provide Compounds IV which upon treatment as described herein will yield the desired Compounds I. Appropriate reactions to accomplish these objectives are well-known and conventional and are within the skill of persons skilled in the art and desired in the literature.

Compounds bearing hydrolyzable ether functions may be prepared in the conventional manner, e.g. a tetrahydrofuran-2-yl, tetrahydropyran-2-yl or 4-methoxytetrahydropyran-4-yl group may be introduced by reacting dihydrofuran, dihydropyran or 4-methoxydihydropyran with a suitable hydroxy-substituted steroidal compound in the presence of an acidic catalyst, such as p-toluene sulfonic acid or phosphorous oxychloride.

Compounds bearing a hydroxy group at positions -3 and/or -17β may be acylated to obtain those compounds wherein any of $R^8$ and/or $R^a$ is acyloxy as defined above. The acylation may be effected by processes known per se for the acylation of steroid alcohols. With respect to compounds having two hydroxy groups, it will be noted that, a hydroxy group at the 3-position is secondary and a hydroxy group at the 17β-position is tertiary. As one skilled in the art will be aware, the ease of acylation is secondary > tertiary and the ease of re-saponification is likewise secondary > tertiary. Accordingly, acylating agents and the stringency of acylating conditions can be chosen depending on the degree of acylation required employing conventional techniques. Suitable acylating agents for the 3-position include organic acids, acyl halides and acid anhydrides of formulae acyl-OH, acyl-Hal and (acyl)₂O, respectively, wherein acyl is a group suitable as $R^8$ or $R^a$, as defined above, and Hal signifies bromine or chlorine, and mixtures thereof. Where the desired acyl moiety is acetyl, a preferred acylating agent is acetic anhydride. In carrying out the acylation, inert solvent may be employed or excess acylating agent may serve as solvent. An acid-binding agent, e.g. pyridine, is preferably used. Preferred temperatures vary between −10° and 50° C. For acylation of both positions, more stringent conditions may be used, characterized by the presence of a strongly acidic catalyst, e.g. p-toluenesulphonic acid. If such catalysts are used, in addition to the above-listed acylating agents, enol acylates, preferably esters of "isopropenyl alcohol," e.g. isopropenyl acetate, may also be employed. The considerations involved are well within the scope of one skilled in the art. However, as the Compounds Ia bear a 17α-substituted-allene function, which may be altered by strong acids, strong acid conditions are preferably avoided. Where a Compound I having a 17β-acetoxy group is required, a preferred acetylating agent is acetic anhydride in which calcium hydride has been suspended. The formation of a 17β-acetoacetyloxy function may be carried out by reacting a compound of Formula Ia with diketene under conventional conditions for such a reaction. The process is suitably effected in an inert organic solvent, such as benzene, toluene or a mixture thereof, and in the presence of a small amount of an organic tertiary amine, e.g. pyridine. The process is conveniently carried out at a relatively low temperature, e.g. from −5° to +35° C.

Ester forms of Compound I may be selectively saponified employing conventional means, e.g. by treatment with methanolic potassium bicarbonate, to obtain a corresponding hydroxy-bearing Compound I. Hence, one skilled in the art can use such knowledge to obtain the desired combination of free hydroxy and acylated positions. Thus, a 3,17β-dihydroxy-bearing steroidal substrate, i.e., a compound of formula I, in which St signifies the structure of formula (1) or (2), in which $R^8$ and $R^a$ both signify a hydrogen atom, may be acylated to obtain either the 3-monoacyloxy or 3,17β-diacyloxy product. By selective hydrolysis (saponification) of the 3,17β-diacyloxy product; as described above, there can be obtained the 3-hydroxy-17β-monoacyloxy product.

Hydrolysis of ketals or protective ether groups may suitably be carried out under strongly acid conditions (Process a), i.e. at a pH value of 3 or lower, e.g. between 1 and 2, using, for example, oxalic acid, p-toluenesulphonic acid or a mineral acid, such as hydrochloric acid, for a relatively short period, e.g. less than 3 hours. Alternatively, the process may be carried out under mild acid conditions, i.e. at a pH value of above 3, preferably from 3 to 5, using, for example, an organic acid such as oxalic acid or acetic acid, for a relatively long period, e.g. in excess of 3 hours. The process may be carried out at a temperature, for example, of from 0° to 100° C., preferably from 15° to 50° C. An inert, water-miscible solvent may be employed, preferably a lower alkanol such as methanol. Where a water-soluble organic acid, which is liquid under the reaction conditions, is employed to create the acid conditions, such may be used in excess to provide the reaction medium. Co-solvents may also be used. As noted above, strong acid conditions are preferably avoided when Compounds Ia are involved.

Persons skilled in the art will appreciate that a Compound I where St is of type (3), (7) or (8), can be rearranged to corresponding compounds where St is of types (1), where $R^7$ is oxo, (5) or (6). Such rearrangement (process b) may suitably be carried out by subjecting the compound of type (3), (7) or (8) to acid or basic conditions. The process may be carried out under either aqueous or nonaqueous conditions.

Basic rearrangement may suitably be effected in an inert organic solvent, such as dioxane, methanol or ethanol. A suitable reaction temperature is from 20° to 120° C., conveniently from 20° to 30° C. or at the reflux temperature of the reaction mixture. Suitable reaction times vary, for example, from ¼ hr. to 6 hrs. Aqueous basic conditions may conveniently be obtained by using, for example, aqueous sodium or potassium hydroxide, preferably at a concentration of from 0.01N to 2N. Where non-aqueous conditions are employed,, the basic conditions are conveniently provided by using an alkali metal lower alkoxide, e.g. sodium methoxide.

Acid rearrangement may suitably carried out under the conditions described above in connection with process (a). However, the aqueous nature of the conditions, essential in process (a), are not essential in the present process and, accordingly, the solvent need not be water-miscible. In reactions involving Compounds Ia, it is as noted above, preferred to avoid strong acids, hence, acid hydrolysis is preferably carried out under mild conditions described above (in connection with process (a), and rearrangement (process (b) is preferably carried out under basic conditions.

As noted above, a 3-hydroxy group of a Compound Ia can be converted to a 3-keto function by treatment with an oxidizing agent conventionally employed in oxidizing an allylic secondary hydroxy group to a keto group, e.g. a quinone, such as p-benzoquinone, chloranil or 2,3-dichloro-5, 6-dicyanobenzoquinone (DDQ), or activated manganese dioxide, e.g. at from 10° to 50° C, preferably at 20° to 30° C. in an inert solvent, e.g. a cyclic ether such as dioxane, or a tertiary alkanol, such as t-butanol. This procedure (process D) thus provides a means for obtaining a 3-oxobearing compound I, by oxidizing the 3-hydroxy function of a compound of formula XI

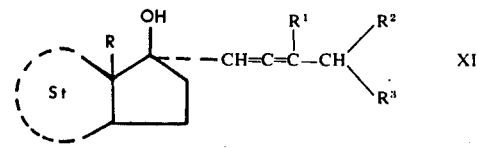

in which R, $R^a$, $R^1$, R and $R^3$ are as defined above, and St' is a gonene residue of formula

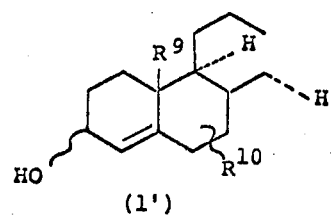

(1')

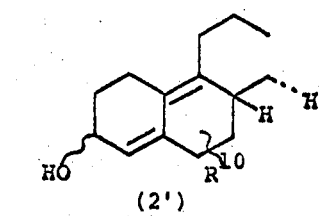

(2')

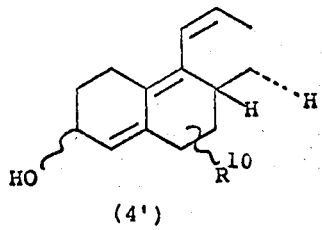

(4')

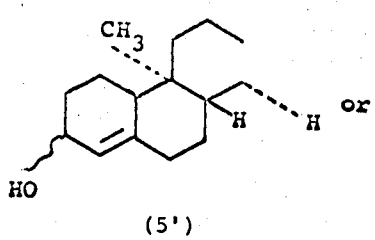

(5')

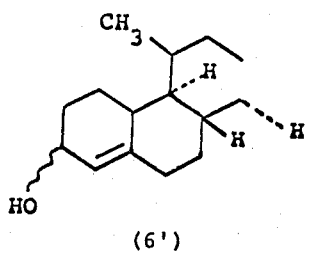

(6')

in which $R^9$ and $R^{10}$ are as defined above, and the wavy line attached to the hydroxy group signifies that such group is in an α- or β-relative position.

Application of process D to compounds XI of St' types (1'), (2'), (4'), (5') and (6'), thus provides the corresponding compounds I of St types (1) or (2) wherein $R^7$ is oxo or (4), (5) or (6), respectively.

Reagents and starting materials employed in the above-described reactions are known, or where not known may be obtained by methods analogous to those for preparing known compounds, many being commercially available.

As noted above, in performing the processes for the production of compounds I, and particularly in performing process (A), above, the reaction conditions employed may be such as to cause undesirable modification in the compounds. In order to avoid such modification, protection techniques may be employed, which techniques are well documented in the literature. For example, keto functions at the 3-position may be protected by conversion to ketal functions, such as bisdimethoxy, ethylenedioxy and propylenedioxy functions and hydroxy functions to tetrahydropyranyloxy, 4-methoxy-tetrahydropyranyloxy or tetrahydrofuranyloxy functions, being reconverted in conventional manner, e.g. by acid hydrolysis, after subjection to the "modifying" reaction conditions. The use of such protection and deprotection techniques in performing the processes of the invention are intended to be embraced by the present invention. On the other hand, where modification does occur and yet a desired compound I is obtained, protection techniques need not be employed. For example, if in process (A) it is desired to obtain a compound in which St has structure (1), in which $R^7$ signifies a hydroxy group, such can be obtained by using a compound of formula II in which $R^7$ signifies a keto function, the keto function being reduced under the reaction conditions to a hydroxy group if not protected.

Indeed, protection of the keto function need not be carried out in process (A), even if a keto bearing final compound is desired, where process (A) is followed by reoxidation to the keto function. Thus, non-protection of a 3-oxo bearing compound of formula II, when subjected to the reaction conditions of process (A), will tend to lead to production of a compound of formula XI.

As will be appreciated, in the compounds of formula I, the carbon atom bearing groups $R^2$ $R^3$ is assymetrical when $R^2$ and $R^3$ are dissimilar. Hence, optical isomers of compounds of formula I are possible and when $R^1$ is not the same as $-CHR^2R^3$ geometric isomers are possible. Such isomers may be separated by conventional means, for example, by fractional crystallization of counter current distribution. Such isomers are embraced by the present invention.

Compounds I of this invention are useful because they possess pharmacological properties in animals. In particular, the compounds are useful as fertility control agents in warm-blooded animals, e.g. mammals, and in regulating estrus or menstrual function as they have progestational activity. The progestational activity of said compounds is indicated by the well-known Clauberg test involving observation of uterine changes in immature female white rabbits given from about 0.001 to 1 milligram of the compound being tested. Various compounds I exhibit estrogenic activity in addition to the above-mentioned progestational activity. The estrogenic activity is indicated in the rat as determined by wellknown methods, e.g., the method basically described in Am. J. Physiol. 189 (1957) 355.

For the above-mentioned uses Compounds I may be combined with a pharmaceutically acceptable carrier or adjuvant. They may be administered orally or parenterally. The dosage will vary depending upon the mode of administration utilized and the particular compound employed. However, in general, satisfactory results are obtained when the compounds are administered at a daily dosage of from about 0.001 milligram to 30 milligrams. This daily dosage may be administered in sustained release form. As will be appreciated by those skilled in the art, the daily dosage level is recognized as not directly related to body weight. Dosage forms suitable for internal administration comprise from about 0.001 mg. to 30 mg. of the compound in admixture with a solid or liquid pharmaceutical carrier or diluent; solid forms, e.g. capsules or tablets being preferred.

In general, the compounds I of the type (2) form a class of compounds of interest from the standpoint of progestational activity. In this class of type (2) compounds particular mention may be made of the compounds in which $R^1$ and $R^3$ are joined to constitute a polymethylene bridge of from 1 to 4 carbon atoms, preferably 3 to 4 carbon atoms, more preferably where $R^2$ is a hydrogen atom. In this class of type (2) compounds, particular mention may also be made of the compounds in which $R^2$ is hydrogen or alkyl and $R^3$ is hydrogen or alkyl and $R^2$ and $R^3$ do not total more than 4 carbon atoms, preferably those in which $R^2$ is hydrogen or R¹ is hydrogen, more preferably with both R¹ and R² being hydrogen. Within this subclass of type (2) compounds there is also mentioned those in which R³ is alkyl of 1 to 3 carbon atoms which compounds exhibit potent progestational activity with very little or essentially no estrogenic activity. Again these compounds of type (2) in which R³ is alkyl of 1 to 3 carbon atoms also preferably have R² being hydrogen or R¹ being hydrogen, more preferably both R¹ and R² being hydrogen. Special mention may be made, for example, of the compound 17α-(penta-1',2'-dienyl)-estra-4,9-dien-17β-ol-3-one because of its very high level of progestational activity coupled with at most very little estrogenic activity. On the other hand, the compounds of type (2) in which R² and R³ are hydrogen and preferably R¹ is also hydrogen, such as 17α-(buta-1',2'-dien-1'-yl)-estra, 4,9-dien-17β-ol-3-one, exhibit strong estrogenic activity in combination with the progestational activity. With respect to all of the above-indicated class or sub-class of the type (2) compound it is preferred that these compounds also have any one or more than more preferably all of the following additional features: (a) R⁷ equal oxo; (b) R¹⁰ equal hydrogen; and (c) R$^a$ equal hydrogen.

Another group of compounds of the formula 1 of interest are those of the type (1). Mention may be made, for example, of the compounds of type (1) in which R² and R³ are each hydrogen or alkyl because of the definite estrogenic activity component of compounds representing this sub-class. With respect to these compounds of type (1) in which R² and R³ total no more than 4 carbon atoms and it generally more preferred that those compounds also have any one or more, and desirably all of the following features: (a) R⁹ equal hydrogen; (b) R¹⁰ equal hydrogen; (c) R² equal hydrogen; (d) R$^a$ equal hydrogen; and (e) R³ equal to alkyl of 1 to 3 carbon atoms. In this sub-class of compounds of the type (1) specific mention may be made of the compounds 17α-(penta-1',2'-dien-yl)-estra-4-en-3β, 17β-diol and 17α-(penta-1',2'-dien-1'-yl)-estra-4-en-17β-ol-3-one because of their combined estrogenic and progestational activity.

The Compounds I may be administered as the sole active ingredient, or if desired, furnished in combination with an estrogenic agent in a manner conventional in the anti-fertility area.

A representative formulation suitable for oral administration is a tablet prepared by standard tabletting techniques which contains the following:

| Ingredient | Parts by Weight |
|---|---|
| 17α-(Penta-1',2'-dienyl)-estra-4,9-dien-17β-ol-3-one | 0.1 |
| Tragacanth | 2 |
| Lactone | 89.4 |
| Corn Starch | 5 |
| Talcum | 3 |
| Magnesium Stearate | 0.5 |

The following examples are provided as illustrative of the present invention. In the examples, all temperatures are Centigrade and room temperature is 20° to 30° C., unless indicated otherwise.

EXAMPLE 1

17α-(Penta-1',2'-dienyl)-estra-4,9-dien-17β-ol-3-one*

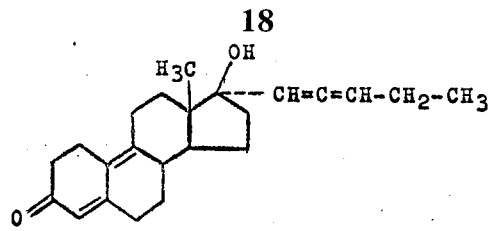

* May also be designated 17α-[1'-(penta-1'-2'-dienyl)]-estra4,9-dien-17β-ol-3-one or 17α-(penta-1',2'-dien-1'-yl)-estra4,9-dien-17β-ol-3-one.

Step A.

17α-(3'-piperidino-pent-1'-ynyl)-estra-4,9-dien-17β-ol-3-one**

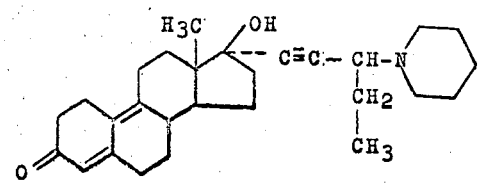

** May also be designated 17α-[3-(1-piperidyl)-1-pentynyl]-estra4,9-dien-17β-ol-3-one.

1.18 g. of 17α-ethynylestra-4,9-dien-17β-ol-3-one is dissolved in 11.8 ml. p-dioxane. To the solution, 100 mg. of cuprous chloride, 464 mg. prioponaldehyde, and 500 mg. piperidine are added. The resulting reaction mixture is stirred at room temperature, water dry nitrogen gas for 24 hrs. The resultant reaction mixture is diluted with 2 ml. water, solids which separate are filtered, and the filtrate evaporated to dryness to obtain a residue. The residue is dissolved in methyl-isobutyl-ketone (MIBK), and washed with water, then brine (saturated aqueous sodium chloride), the solution then dried over anhydrous sodium sulfate, and then evaporated to dryness to obtain 17α-(3'piperidino-pent-1'-ynyl)-estra-4,9-dien-17α-ol-3-one as an oil.

Step B.

17α-[(N-methyl)-3'-piperidinium-pent-1'-ynyl]-estra-4,9-dien-17β-ol-3-one iodide

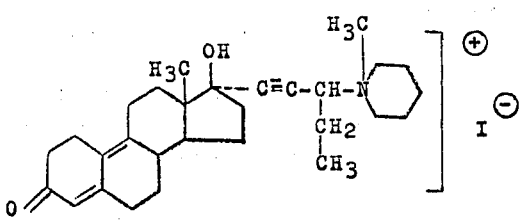

1.3 g. of the product of Step A is dissolved in 13 ml. acetonitrile, and 2.0 ml. of methyl iodide is added. The solution is heated at 35° – 40° C. for 30 minutes, and then diluted slowly with ether. The oil which separates, is washed three times with ether. Residual solvent is then removed from the oil in vacuum to give 17α-[(N-methyl)-3'-piperidinium-pent-1'-ynyl)]-estra-4,9-dien-17β-ol-3-one iodide.*

* May also be designated 17α-[3-(1-piperidyl)-1-pentynyl]-estra-4,9-dien-17β-ol-3-one methiodide.

Step C.

17α-(penta-1',2'-dienyl)-estra-4,9-dien-3,17β-diol

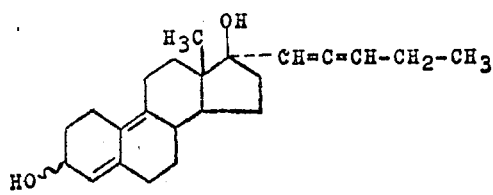

1.6 g. of the quaternary ammonium iodide product of Step B is suspended in 48 ml. of tetrahydrofuran (THF) and 30 ml. of 35% of sodium bis-(2-methoxyethoxy) aluminum hydride in benzene is added to the stirred mixture. Stirring is continued for 3 hrs. To the stirred mixture, 5 ml. of water is added and stirring is continued for 2 hrs. The resulting suspension is then filtered and the filter cake is washed with THF. The combined filtrate and wash is evaporated to dryness. The residue is dissolved in MIBK. The MIBK solution is washed with water, then washed with brine, and then dried over anhydrous sodium sulfate, then is evaporated to dryness to obtain 17α-(penta-1',2'-dienyl)-estra-4,9-dien-3,17β-diol,* as an oil.

* May also be designated 17α-[1'-(penta-1',2'-dienyl)]-estra-4,9-dien-3,17β-diol or 17α-(penta-1',2'-dien-1'-yl)estra-4,9-dien-3,17β-diol.

Step D.

17α-(Penta-1',2'-dienyl)-estra-4,9-dien-17β-ol-3-one 750 mg. of the diol product of Step C is dissolved in 7.5 ml. p-dioxane and a solution of 500 mg. of 2,3-dichloro-5,6-dicyanobenzoquinone (DDQ) in 4.0 ml. of p-dioxane is added to it. The mixture is stirred at room temperature for 1 hr. Separated crystals are filtered, washed with p-dioxane. Filtrate and wash are combined and treated with 15 ml. of 75 ml. of water containing 2% sodium dithionite and 10% potassium carbonate. The resulting mixture is slowly diluted with water. An oil separates and is extracted with ether. The ether solution is washed with water, dried over anhydrous sodium sulfate and the solution is percolated over neutral alumina. The ether solution is evaporated to dryness to obtain a solid residue. The residue is recrystallized from acetone-hexane (1:1), to obtain the title product, m.p. 135° – 137° C.

Repeating the procedure of this example, but using in place of the 17α-ethynylestra-4,9-dien-17β-ol-3-one starting material, equivalent amounts of the compounds of Column A, there is accordingly obtained the respective compounds of Column B:

| A | B |
|---|---|
| a) 17α-ethynylestra-4-en-17β-ol-3-one | a) 17α-(penta-1',2'-dienyl)-estra-4-en-17β-ol-3-one |
| b) 17α-ethynylandrost-4-en-17β-ol-3-one | b) 17α-(penta-1',2'-dienyl)-androst-4-en-17β-ol-3-one |
| c) 17α-ethynyl-9α-methyl-estra-4-en-17β-ol-3-one | c) 9α-methyl-17α-(penta-1',2'-dienyl)-estra-4-en-17β-ol-3-one |
| d) 17α-ethynyl-11β-methyl-estra-4-en-17β-ol-3-one | d) 11β-methyl-17α-(penta-1',2'-dienyl)-estra-4-en-17β-ol-3-one |

EXAMPLE 2

17α-(4'-Methylpenta-1',2'-dienyl)-estra-4,9-dien-17β-ol-3-one*

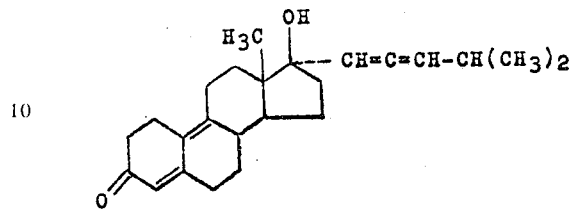

*May also be designated 17α-(4-methyl-1,2-pentadienyl)-4,9-dien-17β-ol-3-one.

Step A.

17α-(4'-Methyl-3'-piperidino-pent-1'-ynyl)-estra-4,9-dien- ** 17β-ol-3-one

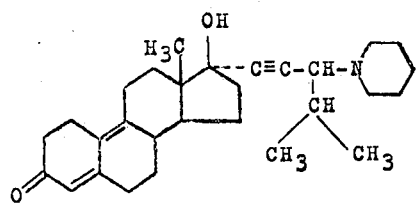

** May also be designated 17α-[3-(1-piperidyl)-4-methyl-1-pentynyl]-estra-4,9-dien-17β-ol-3-one.

5.92 g. of 17α-ethynylestra-4,9-dien-17β-ol-3-one is dissolved in 30 ml. p-dioxane. 300 mg. cuprous chloride is added to the solution. The resulting mixture is heated to 90° – 95° C. under dry nitrogen, and while the mixture is vigorously stirred, a solution of 2.8 g. iso-butyraldehyde-piperidino enamine in 14 ml. p-dioxane is added to it over a period of 5 mins. After the completed addition, the mixture is kept at 95° C. for 10 mins. The mixture is cooled to room temperature and filtered. The filtrate is evaporated to dryness to obtain a residue. The residue is dissolved in a minimum amount of ether, filtered, and the filtrate is evaporated to dryness, giving 17α-(4'-methyl-3'-piperidinopent-1'-ynyl)-estra-4,9-dien-17β-ol-3-one.

Step A'.

17α-(4'-methyl-3'-piperidino pent-1'-ynyl)-estra-4,9-dien-17β-ol-3-one (alternate process)

1.18 g. of 17α-ethynylestra-4,9-dien-17β-ol-3-one is dissolved in 11.8 ml. p-dioxane. To the solution 100 mg. of cuprous chloride, 564 mg. of iso-butraldehyde and 500 mg. of piperidine is added. The resultant mixture is stirred at room temperature for 24 hrs., under dry nitrogen gas. The mixture is then diluted with 2 ml. of water, and solids which separate are filtered off and the filtrate is evaporated to dryness to obtain a residue. The residue is dissolved in MIBK which solution is washed with water, then brine, the solution dried over anhydrous sodium sulfate, and then evaporated to dryness to obtain 17α-(4'-methyl-3'-piperidino-pent-1'-ynyl)-estra-4,9-dien-17β-ol-3-one, as an oil.

Step B.

Methyliodide quaternary ammonium salt of 17α-(4'-methyl-3'-piperidino-pent-1'-ynyl)-estra-4,9-dien-17β-ol-3-one *

*May also be designated 17α-[3-(1'-piperidyl)-4-methyl-1-pentynyl]estra-4,9-dien-17β-ol-3-one methiodide.

8.5 g. of 17α-(4'-methyl-3'-piperidinopent-1'-ynyl)-estra-4,9-dien-17β-ol-3-one is dissolved in 100 ml. acetonitrile and 7.5 ml. methyliodide is added thereto. The solution is heated at 65° to 70° C. for 4 hrs. The solution is cooled to room temperature and slowly diluted with 450 ml. ether. Crystals separate and are filtered and washed with ether, giving methyl iodide quaternary ammonium salt of 17α-(4'-methyl-3'-piperidinopent-1'-ynyl)-estra-4,9-dien-17β-ol-3-one.

Step C.

17α-(4'-Methylpenta-1',2'-dienyl)-estra-4,9-dien-3,17β-diol 10.8 g. of the methyliodide salt of Step B is suspended in 325 ml. of tetrahydrofuran. To the suspension, 24 ml. of 35% sodium bis-(2-methoxyethoxy)-aluminum hydride in benzene-THF (1:1 vol/vol) is added over a period of 5 mins. The reaction mixture is stirred at room temperature for 2.5 hrs., then 64 ml. of water is added portionwise to the mixture and stirring is continued for 2 hrs. The reaction mixture is filtered, the filter cake washed with 100 ml. MIBK. Filtrate and wash are combined and concentrated in vacuo to remove THF. The solution is then diluted with 300 ml. MIBK. The solution is then washed with water, then brine and dried over anhydrous sodium sulfate and is evaporated to dryness, giving 17α-(4'-methylpenta-1',2'-dienyl)-estra-4,9-dien-3,17β-diol.

Step D.

17α-(4'-Methylpenta-1',2'-dienyl)-estra-4,9-dien-17β-ol-3-one 6.5 g. of 17α-(4'-methylpenta-1',2'-dienyl)-estra-4,9-dien-3,17β-diol is dissolved in 65 ml. p-dioxane and at room temperature, a solution of 4.64 g. of DDQ in 46 ml. of p-dioxane is added thereto over a period of 5 mins. The reaction mixture is then stirred for 1.5 hrs. Solids separate and are filtered off and washed with 25 ml. p-dioxane. The combined filtrate and wash are treated with a solution of 2.0 g. sodium dithionite and 10 g. anhydrous potassium carbonate in 75 ml. water. After this, the reaction mixture is slowly diluted with water. Crystals separate and are collected by filtration, and then dissolved in ether. The ether solution is washed with water, then brine and dried over anhydrous sodium sulfate. The solution is then concentrated to 70 ml. volume and percolated over 12 g. of silica gel. The silica gel is washed with ether. The combined ether solution and wash is evaporated to dryness to obtain the title compound as a crystalline residue. The crude title compound is crystallized from acetone-hexane (1:1) giving 17α-(4'-methylpenta-1',2'-dienyl)-estra-4,9-dien-17β-ol-3-one, m.p. 145° – 147° C.

Repeating the procedure of this example but using an equivalent amount of either 17α-ethynylestra-4-en-17β-ol-3-one or 17α-ethynylestra-4,9,11-trien-17β-ol-3-one, in place of the 17α-ethynylestra-4,9-dien-17β-ol-3-one in Step A of this example, there is accordingly obtained 17α-(4'-methylpentyl-1',2'-dienyl)estra-4-en-17β-ol-3-one or 17α-(4'-methylpentyl-1',2'-dienyl)estra-4,9,11-trien-17β-ol-3-one.

EXAMPLE 3

17α-(4'-phenylbuta-1',2'-dienyl)-estra-4,9-dien-17β-ol-3-one

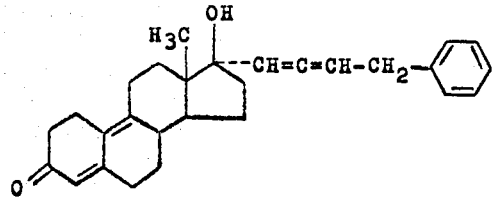

Step A.

17α-(3'-piperidino-4'-phenylbut-1'-ynyl)-estra-4,9-dien-17β-ol-3-one

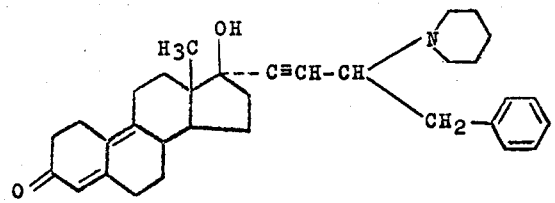

5.92 g. of 17α-ethynylestra-4,9-dien-17β-ol-3-one is dissolved in 30 ml. p-dioxane and 400 mgs. of cuprous chloride is added. The resulting suspension is heated to 100° C. and a solution of 4.0 g. of phenyl acetaldehyde-piperidino-enamine in 14 ml. p-dioxane is added over a period of 10 mins. After completing the addition, heating at 100° C. is continued for 1/2 hr. The mixture is then cooled to room temperature, filtered, and the filtrate is evaporated to a syrup. Residual p-dioxane is then removed under high vacuum. The residue is dissolved in methylenechloride and is charged to a column, containing silica gel. The column is washed with methylene chloride and product is eluted with methanolmethylene chloride (5:95) yielding 17α-(3'-piperidino-4'-phenylbut-1'-ynyl)-estra-4,9-dien-17β-ol-3-one.

Step B.

Methyl p-toluene sulfonate quaternary ammonium salt of 17α-(3-piperidino-4'-phenylbut-1'-ynyl)-estra-4,9-dien-17β-ol-3-one 6.4 g. of 17α-(3'-piperidino-4'-phenylbut-1'-ynyl)-estra-4,9-dien-17β-ol-3-one is dissolved in 15.0 ml. p-toluenesulfonic acid-methylester and the solution is heated at 75° C. for 3 hrs. The solution is then cooled to room temperature and is charged to a column of silica gel. The column is washed with methylene chloride. The product is eluted with methanolmethylene chloride (1:9) to obtain methyl p-toluene sulfonate quaternary ammonium salt of 17α-(3-piperidino-4'-phenylbut-1'-ynyl)-estra-4,9-dien-17β-ol-3-one.

Step C.

17α-(4'-phenylbuta-1',2'-dienyl)-estra-4,9-dien-3,17β-diol 7.0 g. of the quaternary ammonium salt of Step B is suspended in 210 ml. of THF and while stirred, 10 ml. of 35% sodium bis-(2-methoxyethoxy) aluminum hydride in benzene is added. The mixture is stirred at room temperature for 3 hrs. 20 ml. of water is then added and stirring is continued for 2 hrs. The resulting suspension is then filtered and the filtrate is evaporated to dryness to obtain a residue. The residue is dissolved in 200 ml. MIBK, washed with water, dried over anhydrous sodium sulfate and is evaporated to dryness to obtain 17α-(4'-phenylbuta-1',2'-dienyl)-estra-4,9-dien-3,17β-diol.

Step D.

17α-(4'-phenylbuta-1',2'-dienyl)-estra-4,9-dien-17β-ol-3-one 4.0 g. of 17α-(4'-phenylpropa-1',2'-dienyl)-estra-4,9-dien-3,17β-diol is dissolved in 40 ml. dioxane and a solution of 2.6 g. 2,3-dichloro-5,6-dicyanobenzoquinone (DDQ) in 26 ml. dioxane is added at room temperature. The mixture is stirred at room temperature for 3 hrs. A solution of 2.0 g. sodium-dithionite and 5 g. of anhydrous potassium carbonate in 20 ml. water is added. The mixture is stirred for 10 mins. and the solution is then diluted with 50 ml. saturated aqueous sodium chloride (brine). An oil separates and is extracted with ether. The ether solution is washed with water, and dried over anhydrous sodium sulfate and is percolated over 45 g. of silica gel. The ether is removed by evaporation to dryness to give 17α-(4'-phenylbuta-1',2'-dienyl)-estra-4,9-dien-17β-ol-3-one.

EXAMPLE 4

17α-(3',3'-pentamethylenepropa-1',2'-dienyl)-estra-4,9-dien-17β-ol-3-one

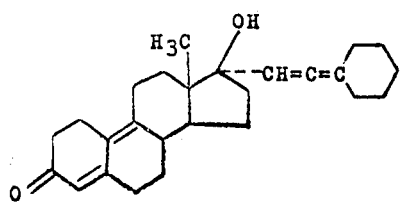

Step A

17α-(3'-N-piperidino-3',3'-pentamethyleneprop-1'-ynyl)-estra-4,9-dien-17β-ol-3-one

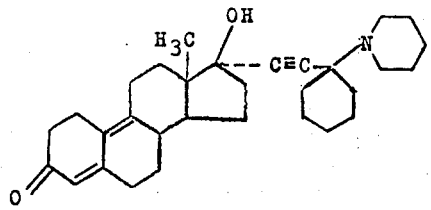

3.0 g. of 17α-ethynylestra-4,9-dien-17β-ol-3-one is suspended in 12.0 ml. C-hexanone-piperidino-enamine and the suspension is heated to 130° C. under dry nitrogen. When steroid dissolves, 180 mgs. of cuprous chloride is added. The stirred mixture is kept at 130° C. for 30 mins. The mixture is cooled to room temperature and is dissolved in methylene chloride. The solution is percolated over silica gel. The silica gel is washed with methylene chloride. The combined methylene chloride is washed and solution is evaporated to dryness and the residual oil washed with petroleum ether to obtain 17α-(3'-N-piperidino-3',3'-pentamethyleneprop-1'-ynyl)-estra-4,9-dien-17β-ol-3-one, which may also be designated as 17α-2-[1-(1-piperidylcyclohexyl)]ethynyl estra-4,9-dien-17β-ol-3-one.

Steps B, C and D.

Treating the product of Step A of this example by procedures analogous to those of Steps B, C and D of Example 3, the title product of this example is obtained, which may also be designated 17α-(2-cyclohexylidenevinyl)-estra-4,9-dien-17β-ol-3-one.

EXAMPLE 5

17α-[1'-(3'-methyl-buta-1',2'-dienyl)]-9α-methylestra-4-en-17β-ol-3-one.

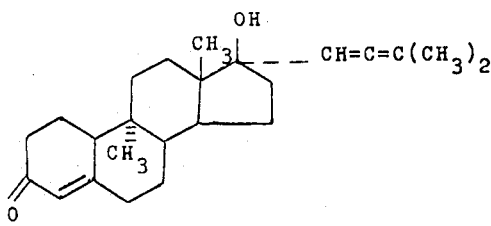

Step A:

17α-[1'-(3'-N-isoindolino-3'-methyl-but-1-ynyl)]-3-methoxy-9α-methylestra-2,5(10)-dien-17β-ol.*

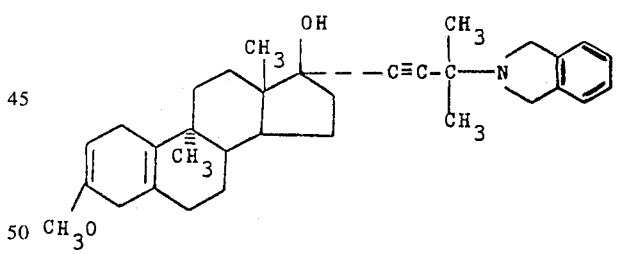

*May also be designated 3-methoxy 17α-[3-(2-isoindolinyl)-3-methyl-1-butynyl]-9α-methylestra-2,5(10)-dien-17β-ol.

To a mixture of 100 mg. of lithium metal in 7 ml. ethylenediamine at 10°C., is added 2.4 g. of 3-(N-isoindolino)-3-methyl-but-1-yne in 12 ml. of tetrahydrofuran. The resulting mixture is stirred at room temperature for 2 hours, then 2.0 g. of 3-methoxy-9α-methylestra-2,5(10)-dien-17-one in 20 ml. of tetrahydrofuran is added and the resulting mixture stirred for 18 hours, and then poured into cold brine (saturated aqueous sodium chloride at about 10°C). The aqueous mixture is then extracted with ether, and the combined ether extracts washed with brine, then dried over anhydrous sodium sulfate, then filtered and evaporated to obtain 17α-[1'-(3-N-isoindolino-3'-methyl-but-1-ynyl)]-3-methoxy-9α-methylestra-2,5(10)-dien-17β-methylestra-2,5(10)-dien-17β-ol.

STEP B:

17α[1'-(3'-N-isoindolino-3'-methyl-but-1-ynyl)]-3-methoxy-9α-methylestra-2,5(10)-dien-17β-ol methyliodide.

To 4.2 g. of 17α-[1'-(3'-isoindolino-3'-methyl-but-1-ynyl)]-3-methoxy-9α-methylestra-2,5(10)-dien-17β-ol in 45 ml. of acetonitrile, is added 4.2 g. of methyliodide, and the mixture heated for 3 hours at 60°C. The mixture is then evaporated under vacuum to obtain the title methyliodide salt.

STEP C:

17α-[1'-(3'-methyl-buta-1', 2'-dienyl)]-9α-methylestra-4-en-17β-ol-3-one.

To 5.1 g. of 17α-[1'-(3'-N-isoindolino-3'-methyl-but-1-ynyl)]-3-methoxy-9α-methylestra-2,5(10)-dien-17β-ol methyliodide (the methyliodide salt of Step C) suspended in 155 ml. of tetrahydrofuran, is added 15 ml. of a 35% benzene solution of sodium dihydro bis-(2-methoxyethoxy) aluminate with stirring, and agitation is continued for 1.5 hours. 1 ml. of methanol and 1 ml. of water are then added to the mixture to decompose excess hydride and the resulting suspension is then filtered. The filtrate is evaporated under vacuum to obtain a residue is dissolved is isopropyl acetate, and washed with water, until wash is neutral. The isopropyl acetate solution is then dried over anhydrous sodium sulfate, filtered and evaporated (under vacuum) to dryness to obtain a residue. The residue is chromatographed on a thin layer silica gel (preparative thin layer chromatography plate; 1 m/m thickness) using methylenechloride as solvent to obtain the title product as an oil (infra red spectrum λ ethanol/max 272 mμ). The title product may also be designated as 17α-[1'-(3'-methyl-buta-1', 2'-dienyl)]-9α-methyl-19-nor-testrosterone, 17α-(3-methyl-1,2-butadienyl)-9α-methylestra-4-en-17β-ol-3-one or 17α-(3-methyl-buta-1',2'-dien-1'-yl)-9α-methylestra-4-en-17β-ol-3-one.

EXAMPLE 6

17α-[1'-(buta-1', 2'-dienyl)]-9α-methylestra-4-en-17β-ol-3-one

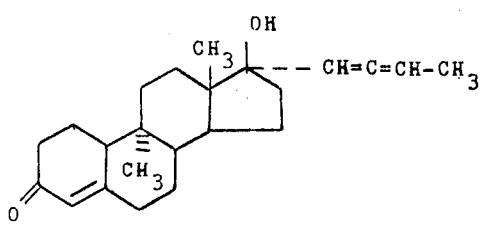

STEP A:

17α-[1'-(3'-N-isoindolino-but-1-ynyl)]-3-methoxy-9α-methylestra-2,5(10)-dien-17β-ol.

To a mixture of 0.5 g. of lithium metal in 35 ml. of ethylenediamine, at 10°C., is added 10.4 g. of 3-(N-isoindolino)-but-1-yne in 52 ml. of tetrahydrofuran. The resulting mixture is stirred at room temperature for 1 hour, then 10g. of 3-methoxy-9α-methylestra-2,5(10)-dien-17-one in 100 ml. of tetrahydrofuran is added and the resulting mixture stirred for 18 hours, and then poured into cold brine. The resulting aqueous mixture is then extracted with ether, and the combined ether extracts washed with brine, dried over anhydrous sodium sulfate, then filtered and evaporated to obtain 17α-[1'-(3'-N-isoindolino-but-1'-ynyl)]-3-methoxy-9α-methylestra-2,5(10)-dien-17β-ol which may also be designated 3-methoxy-17α-[3-(2-isoindolinyl)-3-methyl-1-butynyl]-9α-methylestra-2,5(10)-dien-17β-ol.

STEP B:

17α-[1'-(3'-N-isoindolino-but-1-ynyl)]-3-methoxy-9α-methylestra-2,5(10)-dien-17β-ol methiodide.

To 20 g. of 17α-[1'-(3'-N-isoindolino-but-1-ynyl)]-3-methoxy-9α-methylestra-2,5(10)-dien-17β-ol is 210 ml. of acetonitrile is added 21 ml. of methyl iodide, and the resulting mixture heated for 2 hours at 60°C. The mixture is then evaporated under vacuum to obtain the title methiodide salt as a residue.

STEP C:

17α-[1'-(buta-1', 2'-dienyl)]-3-methoxy-9α-methylestra-2,5(10)-dien-17β-ol.

28 g. of the methiodide salt obtained in Step B is suspended in 870 ml. of tetrahydrofuran and while the suspension is vigorously stirred, 84 ml. of a 35% benzene solution of sodium dihydro bis-(2-methoxyethoxy) aluminate is added, and the resulting mixture agitated for 18 hours. 5ml. of methanol is then added to decompose excess hydride reagent. The mixture is filtered and the filtrate evaporated to dryness under vacuum to obtain a residue. The residue is dissolved in a sufficient amount of isopropyl acetate, and the isopropyl acetate solution washed with water, until the wash is neutral, then dried over anhydrous sodium sulfate, filtered and evaporated to dryness to obtain an oily residue. which is then dissolved in methylene chloride. The methylene chloride solution is then percolated over silica gel, filtered and evaporated to obtain as a residue 17α-[1'-(buta-1', 2'-dienyl)]-3-methoxy-9α-methylestra-2,5-(10)-dien-17β-ol.

STEP D:

17α-[1'-(buta-1', 2'-dienyl)]-9α-methylestra-4-en-17β-ol-3-one.

To 4.1 g. of 17α[1'-buta-1', 2'-dienyl)]-3-methoxy-9α-methylestra-2,5(10)-dien-17β-ol. in 80 ml. of glacial acetic acid is added 15 ml. of water to obtain a solution which is allowed to remain at room temperature for 3 hours. The solution is then diluted with 600 ml. water and extracted with isopropyl acetate. The extract is decolorized with charcoal, filtered, and then washed with brine until the wash is neutral. The isopropyl acetate extract is then dried over anhydrous sodium sulfate, filtered, and evaporated to dryness to obtain the title product as residue, which may be refined by crystallization from ether, m.p. 137°–141°C. (λ ethanol/max 241 mμ). The title product may also be designated 17α-[2'-(buta-1',2'-dienyl)]-9α-methyl-19-nortestosterone, or 17α-(buta-1',2'-dien-1'-yl)-9α-methylestra-4-en-17β-ol-3-one.

EXAMPLE 7

17α-(2-cyclododecylenevinyl)-estra-4,9-dien-17β-ol-3-one

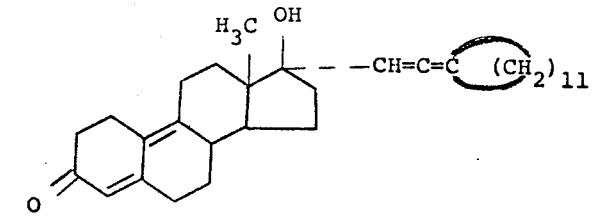

STEP A:
3,3-Ethylenedioxy-17α-1-(2-tetrahydropyran-2-yloxycyclododecyl)-ethynylestra-5(10),9(11)-dien-17β-ol.

To a cooled (0°–5°), sterred solution of 5.1 g. of 1-ethynyl-1-(tetrahydropyran-2-yloxy)-cyclododecane in 25 ml. of THF under nitrogen, is added 11.0 ml. of a 1.6 M. solution of n-butyl lithium in hexane. This solution is stirred at 0° for 30 minutes and then a solution of 5.0g. of 3,3-ethylenedioxyestra-5(10),9(11)-dien-17-one in 25 ml. of THF is added. The reaction mixture is then allowed to warm to room temperature and stirred at this temperature under nitrogen for about 16 hours. The cooled (ice) mixture is then poured onto ice (about 100 g.) and 50 ml. of a 10° sodium bicarbonate solution and 100 ml. of brine. The mixture is extracted three times with 50 ml. portions of ether and the combined extracts are washed with water and brine before being dried over anhydrous sodium sulfate. Removal of the solvent gives 3,3 ethylenedioxy-17α-1-(2-tetrahydropyran-2-yloxycyclododecyl)ethynylestra-5(10),9(11)-dien-17β-ol as an oil, characterized by its IR spectrum, which shows no absorption characteristic of the 17-carbonyl group.

STEP B:
3,3-Ethylenedioxy-17α-(2-cyclododecylvinyl)-estra-5(10),9(11)-dien-17β-ol To a cooled (0° to 5°) solution of 9.7 g. of the product of Step A, above in 100 ml. of ether stirred under nitrogen is added over 5 minutes, 11.7 ml. of a 4.1 M solution of lithium aluminum hydride in ether, further diluted with ether to a total volume of 25 ml. When the addition is complete, the reaction mixture is allowed to warm to room temperature where it is stirred for 3 hours. It is then cooled in ice and a saturated brine solution is carefully added until all foaming ceases. The precipatate is filtered off and the filtrate is extracted three times with ether. The combined extracts are washed with water and dried over anhydrous sodium sulfate. Removal of the solvent gives a residue which is chromatographed on silica gel. Elution with methylene chloride gives an oil which is crystallized from hexane/ether (10/1) to give 3,3-ethylenedioxy-17α-(2-cyclododecylvinyl)-estra-5(10),9(11)-dien-17β-ol. m.p. 118°–122°.

STEP C:
17α-(2-cyclododecylenevinyl)-estra-4,9-dien-17β-ol-3-one

To a solution of 1.2 g. the product of Step B, above, in 25 ml. of methanol, maintained at 30° to 40°, is added 4 drops of concentrated hydrochloric acid. The temperature is maintained for a further 30 minutes, then the solution is cooled and poured onto ice. The organic material is extracted with ether and the ether solution is washed and dried over anhydrous sodium sulfate. Removal of the ether gives a residue which is applied to thick-layer plates of silica gel. After development of the plates, twice, with chloroform the strongly U.V. absorbing band is removed and eluted with ethyl acetate. Filtration and concentration of the ethyl acetate solution gives a residue which is crystallized from acetone/hexane, (1/1) to yield, the title product, m.p. 159°–161°.

Example 8

Repeating the procedure of Steps A, B, D and D of Example 2, but using in place of the iso-butyraldehydepiperidino enamine starting material used in Step A thereof, an equivalent amount of aldehyde-piperidino enamine, proposed from the aldehyde:
 a. n-butyraldehyde,
 b. n-pentylaldehyde,
 c. n-hexylaldehyde,
 d. n-decylaldehyde, or
 e. 3-methyl-butyraldehyde.
there is obtained
 a. 17α-(n-hexa-1',2'-dien-1'-yl)-estra-4,9-dien-17β-ol-3-one; m.p. acetone-hexane (5/1), 150°–152°C.,
 b. 17α-(n-hepta-1',2'-dien-1'-yl)-estra-4,9-dien-17β-ol-3-one; m.p. acetone-hexane (5/1), 128°–130°C.,
 c. 17α-(n-octa-1',2'-dien-1'-yl)-estra-4,9-dien-17β-ol-3-one; oil,
 d. 17α-(n-dodeca-1',2'-dien-1'-yl)-estra-4,9-dien-17β-ol-3-one, oil, or
 e. 17α-(5'-methyl-hexa-1',2'-dien-1'-yl)-estra-4,9-dien-17β-ol-3-one; acetone-hexane (5/1), m.p. 112'–122°C.

Example 9

Repeating the procedures of Steps A, B, C and D of Example 4, but using in place of the c-hexanone-piperidino-enamine, starting material used in Step A, thereof, an equivalent amount of:
 a. c-pentanone-piperidino-enamine, or
 b. diethyl ketone-piperidino-enamine there is obtained
 a. 17α-(3'-3'-tetramethylene-propa-1',2'-dien-1'-yl)-estra-4,9-dien-17β-ol-3-one,* m.p. 135°–137°C. from ether, or

*May also be designated 17α-(2-cyclopenylidenevinyl)-estra-4,9-dien-17β-ol-3-one.

b. 17α-(3'-ethyl-penta-1',2'-dien-1'-yl)-estra-4,9-dien-17β-ol-3-one.**

**May also be designated 17α-[1'-(3'-ethyl-penta-1',2'-dien-1'-yl)]-estra-4,9-dien-17β-ol-3-one.

EXAMPLE 10

Repeating the procedure of Steps A, B, C and D of Example 2, but in Step A, using in place of the 17α-ethynylestra-4,9-dien-17β-ol-3-one, used therein an equivalent amount of a compound of column A below, and in place of the isobutyraldehyde-piperidino enamine, an equivalent amount of n-propionaldehyde-piperidino enamine, there is obtained the product of column B, below:

| A | B |
|---|---|
| a) 17α-ethynyl-9α-methylestra-4-en-17β-ol-3-one, | a) 9α-methyl-17α-(penta-1',2'-dien-1'-yl)-estra-4-en-17β-ol-3-one, |
| b) 17α-ethynylestra-4-en 17β-ol-3-one, or | b) 17α-(penta-1',2'-dien-1'-yl)-estra-4-en-17β-ol-3-one m.p. from acetone-hexane, (5/1). 103–106°C., or |
| c) 13-ethyl-17α-ethynylgona-4-en-17β-ol-3-one | c) 13-ethyl-17α-(penta-1',2'-dien-1'-yl)-gona-4-en-17β-ol-3-one. |

EXAMPLE 11

17α-[1'-(buta-1',2'-dienyl)]-9α-methyl-estra-4-en-17β-ol-3-one.

Step A:

17α-[1'-(buta-1',2'-dienyl)]-9α-methyl-estra-5(10)en-17β-ol-3-one 4.1 g. of 17α-[1'-(buta-1',2'-dienyl)]-3-methoxy-9α-methyl-estra-2,5(10)-dien-17β-ol is dissolved in 80 ml. of glacial acetic acid and 15 ml. of water is added. The solution is kept at room temperature for 1 hour. The reaction mixture is then diluted with 600 ml. water and is extracted with isopropyl-acetate. The extract is washed with brine, until wash is neutral. The extract is dried over anhydrous sodium sulfate and evaporated to dryness to give 17α-[1'-(buta-1',2'-dienyl)]-9α-methyl-estra-5(10)-en-17β-ol-3-one.

Step B:

17α-[1'-(buta-1',2'-dienyl)]-9α-methyl-estra-4-en-17β-ol-3-one 2.0 g. of 17α-[1'-(buta-1',2'-dienyl)]-9α-methyl-estra-5(10)-en-17β-ol-3-one (obtained in Step A, above) is dissolved in 30 ml. methanol and 3 ml. of 2N sodium hydroxide solution is then added to it under nitrogen gas. The mixture is then heated to 40°–45°C. for 30 minutes. The solution is cooled to room temperature and is neutralized with 2N acetic acid. Most of the methanol is then removed under vacuum and the mixture is diluted with water, then extracted with isopropyl acetate. The extract is washed with water, and is dried over anhydrous sodium sulfate. The solution is evaporated to dryness to obtain a residue which is crystallized from ether to give title compound, m.p.: 137°–141°C.

EXAMPLE 12

3β-Acetoxy-17α-(penta-1',2'-dien-1'-yl)-estra-4-en-17β-ol 0.8 g. of 17α-(penta-1',2'-dien-1'-yl)-estra-4-en-3β,17β-diol is dissolved in 13.0 ml. of pyridine. 4.4 ml. of acetic anhydride is added to the solution, and the solution is allowed to stand at room temperature for 18 hours. The mixture is then poured into 100 ml. of water and extracted 5 times with 10 ml. portions of methylene chloride. The combined methylene chloride extracts are dried over anhydrous sodium sulfate and the solvent removed by evaporation under vacuum to obtain the title compound as residue.

EXAMPLE 13

17α-(Buta-1',2'-dien-1'-yl)-estra-4,9-dien-17β-ol-3-one

Following the procedure of Steps A, B, and C of Example 6, but replacing the 3-methoxy-9α-methylestra-2,5(10)-dien-17-one used therein with an equivalent amount of 3,3-ethylenedioxyestra-5(10),9(11)-dien-17-one, there is obtained 3,3-ethylenedioxy-17α-(buta-1',2'-dien-1'-yl)-estra-5(10),9(11)-dien-17β-ol.

Repeating the procedure of Steps A and B of Example 11, but replacing the 17α-(buta-1',2'-dien-1'-yl)-3-methoxy-9α-methylestra-2,5(10)-dien-17β-ol used therein with an equivalent amount of 3,3-ethylenedioxy-17β-(buta-1',2'-dien-1'-yl)-estra-5(10),9(11)-dien-17β-ol, there is obtained the title product.

Repeating the procedure of Step C of Example 7, but replacing the 3,3-ethylenedioxy-17α-(2-cyclododecylvinyl)-estra-5(10),9(11)-dien-17β-ol, used therein with an equivalent amount of 3,3-ethylenedioxy-17α-(buta-1',2'-dien-1'-yl)-estra-5(10),9(11)-dien-17β-ol or 17α-(buta-1',2'-dien-1'-yl)-estra-(5(10),9(11)-dien-17β-ol-3-one there is likewise obtained the title product.

Alternatively, prolonged treatment with 90% aqueous acetic acid, of 3,3-ethylenedioxy-17α-(buta-1',2'-dien-1'-yl)-estra-5(10),9(11)-dien-17β-ol or 17α-(buta-1',2'-dien-1'-yl)-estra-5(10),9(11)-dien-17β-ol-3-one likewise yields the title product.

EXAMPLE 14

Tablets and capsules containing the ingredients indicated below may be prepared by conventional techniqus and are useful in controlling fertility in the manner described above:

| Ingredients | Tablet (a) | Tablet (b) | Capsule (c) | Capsule (d) |
|---|---|---|---|---|
| 17α-(penta-1',2'-dienyl)-estra-4,9-dien-17β-ol-3-one | 0.1 | 0.5 | 0.5 | 6 |
| Tragacanth | 2 | 10 | — | — |
| Lactose | 89.4 | 247.0 | 299.5 | 494 |
| Corn Starch | 5 | 25 | — | — |
| Talcum | 3 | 15 | — | — |
| Magnesium stearate | 0.5 | 2.5 | — | — |
|  | 100 | 300.0 | 300.0 | 500 |

EXAMPLE 15

The following pharmaceutical composition is formulated with the indicated amount of active agent using conventional techniques. The injectable suspension represents a formulation useful in controlling fertility in the manner described above.

| Ingredients | Weight % |
|---|---|
| 17α-(penta-1',2'-dienyl)-estra-4,9-dien-17β-ol-3-one | 1.0 |
| Sodium alginate | 0.5 |
| Lecithin | 0.5 |
| Sodium chloride | as desired |
| Buffer agent to adjust pH for desired stability | as desired |
| Water | to desired volume |

EXAMPLE 16

Tablets and capsules containing the ingredients indicated below may be prepared by conventional techniques and are useful in controlling fertility and controlling and regulating estrus in large domestic mammals in the manner described above given daily to said host.

| Ingredients | Weight (mg.) | | |
|---|---|---|---|
| | (a) Tablet | (b) Capsule | (c) Capsule |
| 17α-(penta-1',2'-dienyl)-estra-4,9-dien-17β-ol-3-one | 6 | 6 | 10 |
| Tragacanth | 10 | — | — |
| Lactose | 241.5 | 294 | 490 |
| Corn Starch | 25 | — | — |
| Talcum | 15 | — | — |
| Magnesium stearate | 2.5 | — | — |
| Total | 300.0 mg. | 300. mg | 500. mg. |

EXAMPLE 17

Following the procedure of Steps A, B, C and D of Example 1, but using in place of the 17α-ethynylestra-4,9-dien-17β-ol-3-one used therein, an equivalent amount of:

a 6α-methyl-17α-ethynylestra-4-en-17β-ol-3-one.
b 17α-ethynyl-13-n-propylgona-4-en-17β-ol-3-one;
c 7α-methyl-17α-ethynylestra-4,9-dien-17β-ol-3-one;
d 17α-ethynyl-13-ethylgona-4,9-dien-17β-ol-3-one; or
e 17α-ethynyl-13-ethyl-9α-methylgona-4-en-17β-ol-3-one; there is similarly obtained;

a 6α-methyl-17α-(penta-1',2'-dien-1'-yl)-estra-4-en-17β-ol-3-one;
b 13-n-propyl-17α-(penta-1',2'-dien-1'-yl)-gona-4-en-17β-ol-3-one;
c 7α-methyl-17α-(penta-1',2'-dien-1'-yl)-estra-4,9-dien-17β-ol-3 1one;
d 13-ethyl-17α-(penta-1',2'-dien-1'-yl)-gona-4,9-dien-17β-ol-3-one; or
e 17α-(penta-1',2'-dien-1'-yl)-13-ethyl-9α-methylgona-4-en-17β-ol-3-one.

EXAMPLE 18

Following the procedure of Steps A, B and C of Example 1 but using in place of the 17α-ethynylestra-4,9-dien-17β-ol-3-one used therein, an equivalent amount of:

a 17α-ethynylestra-4,9-dien-3β,17β-diol;
b 17α-ethynyl-3-tetrahydropyran-2-yloxyestra-4-en-17β-ol;
c 17α-ethynyl-3-(4-methoxytetrahydropyran-4-yloxy)estra-4,9-dien-17β-ol; or
d 17α-ethynylestra-4-en-3β,17β-diol; there is similarly obtained:

a 17α-(penta-1',2'-dien-1'-yl)-estra-4,9-dien-3β,17β-diol;
b α-(penta-1',2'-dien-1'-yl)-3-tetrahydropyran-2-yloxyestra-4-en-17β-ol;
c 3-(4-methoxytetrahydropyran-4-yloxy)-17α-(penta-1',2'-dien-1-yl)-estra-4,9-dien-17β-ol; or
d 17α-(penta-1',2'-dien-1'-yl)-estra-4-en-3β,17β-diol.

EXAMPLE 19

17α-(4'-Methylpenta-1',2'-dien-1'-yl)-estra-4,9-dien-17β-ol-3-one.

Following the procedure of Steps A, B, C and D of Example 2, but using in place of the cuprous chloride used in Step A thereof, and the same amount of finely powdered copper, there is similarly obtained the title product.

EXAMPLE 20

17α-(Penta-1',2'-dien-1'-yl)-estra-4-en-3β,17β-diol. Repeating the procedure of Steps A, B and C of Example 2, but in a Step A using in place of the 17α-ethynylestra-4,9-dien-17β-ol-3-one, used therein an equivalent amount of 17β-ethynylestra-4-en-3β,17β-diol and in place of the isobutyraldehyde-piperidino enamine, an equivalent amount of n-propionaldehyde-piperidino enamine, there is obtained 17α-(penta-1',2'-dien-1'-yl)-estra-4-en-3β,17β-diol m.p. from acetone-hexane (5/1), 95°–97°C.

What is claimed is:
1. A compound of the formula

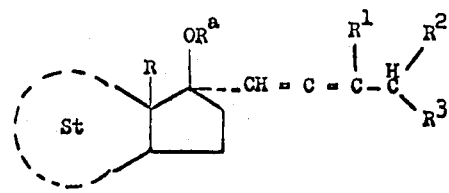

wherein R is alkyl having from 1 to 4 carbon atoms;
$R^a$ is a hydrogen atom, or the residue of a hydrolyzable ether or ester;
$R^1$ is a hydrogen atom or alkyl having from 1 to 6 carbon atoms,
$R^2$ is a hydrogen atom or alkyl having from 1 to 8 carbon atoms,
$R^3$ is a hydrogen atom, alkyl having from 1 to 8 carbon atoms, phenyl, or phenyl having one or two substituents, independently, from the group of fluoro or alkyl having from 1 to 6 carbon atoms; or
$R^1$ and $R^3$ may be joined so as to form a polymethylene bridge having from 3 to 12 carbon atoms; and
St is a gonene residue selected from the group consisting of:

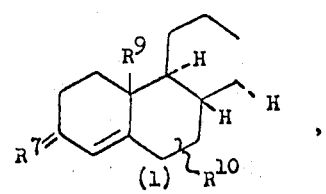

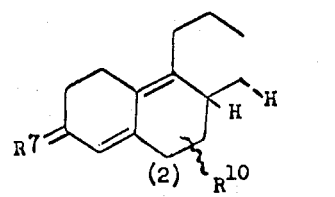

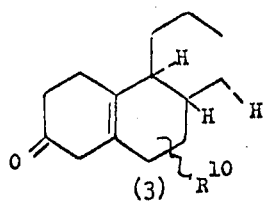
(3)

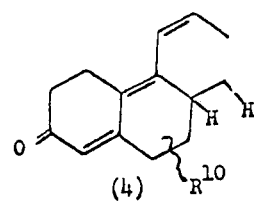
(4)

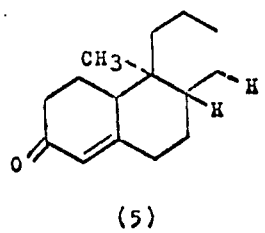
(5)

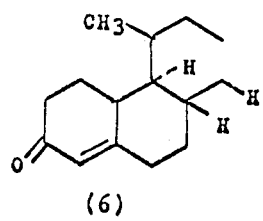
(6)

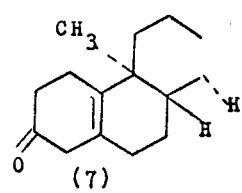
(7)

and

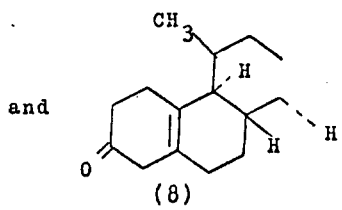
(8)

$R^7$ is oxo or

$R^8$ is a hydrogen atom, a hydrolyzable ether or ester residue;

$R^9$ is a hydrogen atom or methyl; and $R^{10}$ is a hydrogen atom, 6α-methyl or 7α-methyl, provided that when any of $R^2$ and $R^3$ is a hydrogen atom or alkyl, $R^1$ is a hydrogen atom and the total number of carbon atoms in $R^2$ and $R^3$ does not exceed 4, then St is not of type (2).

2. A compound of claim 1 wherein $R^a$ is a hydrogen atom.

3. A compound of claim 2 wherein St is of type (1).

4. The compound of claim 3 which is 17α-(penta-1',-2'-dien-1'-yl)estra-4-en-17β-ol-3-one.

5. The compound of claim 3 which is 17α-(penta-1',-2'-dien-1'-yl)-estra-4-en-3β,17β-diol 6. A compound of claim 2 wherein St is of type (2).

7. A compound of claim 6 which is 17α-(4'-phenyl-buta-1',2'-dien-1'-yl)-estra-4,9-dien-17β-ol-3-one.

8. The compound of claim 6 which is 17α-(2-cyclopentylidenevinyl)-estra-4,9-dien-17β-ol-3-one.

9. The compound of claim 6 which is 17α-(2-cyclohexylidenevinyl)-estra-4,9-dien-17β-ol-3-one.

10. The compound of claim 6 which is 17α-(2-cyclododecylenevinyl)-estra-4,9-dien-17β-ol-3-one.

11. The compound of claim 6 which is 17α-(dodeca-1',2'-dien-1'-yl)-estra-4,9-dien-17β-ol-3-one.

12. The compound of claim 6 which is 17α-(1'-[3'-ethyl-penta-1',2'-dien-1'-yl)]-estra-4,9-dien-17β-ol-3-one.

13. A compound of claim 2 wherein St is of type (5).

14. The compound of claim 13 which is 17α-(buta-1',2'-dien-1'-yl)-9α-methylestra-4-en-17β-ol-3-one.

15. The compound of claim 13 which is 17α-[1'-(3'-methyl-buta-1',2'-dien-1'-yl)]-9α-methylestra-4-en-17β-ol-3-one.

16. The compound of claim 13 which is 9α-methyl-17α-(penta-1',2'-dien-1'-yl)-estra-4-en-17β-ol-3-one.

17. A compound of claim 1 wherein each of $R^1$ and $R^2$ is, independently, a hydrogen atom or alkyl having from 1 to 6 carbon atoms;

$R^3$ is a hydrogen atom, alkyl having from 1 to 6 carbon atoms, phenyl, or phenyl having one or two fluoro or alkyl substituents having from 1 to 6 carbon atoms; or $R^1$ and $R^3$ may be joined so as to form a polymethylene bridge having from 3 to 5 carbon atoms; and St is a gonene residue selected from the group consisting of:

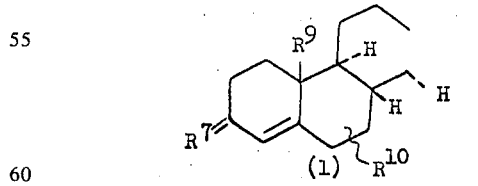
(1)

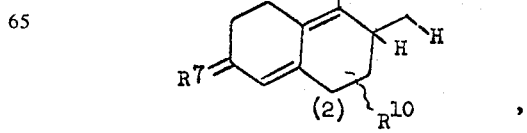
(2)

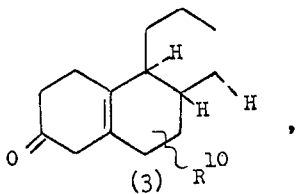

(3)

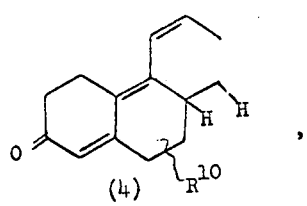

(4)

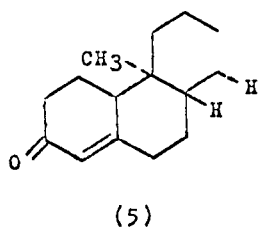

(5)

and

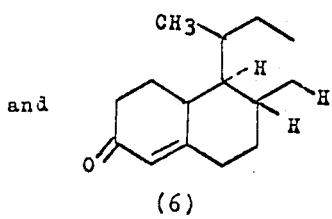

(6)

wherein R⁷ is oxo or

18. A compound of claim 17 wherein R" is a hydrogen atom.

19. A compound of claim 18 wherein R" is a hydrogen atom, St is of type (2).

20. A compound of claim 1 wherein St is of type (1).
21. A compound of claim 1 wherein St is of type (2).
22. A compound of claim 1 wherein St is of type (3).
23. A compound of claim 1 wherein St is of type (4).
24. A compound of claim 1 wherein St is of type (5).
25. A compound of claim 1 wherein St is of type (6).
26. A compound of claim 1 wherein St is of type (7).
27. A compound of claim 1 wherein St is of type (8).
28. A compound of claim 21 wherein each of R² and R³, independently, is a hydrogen atom or alkyl.
29. A compound of claim 28 wherein the total number of carbon atoms of R² plus R³ does not exceed 4.
30. A compound of claim 29 wherein R³ is alkyl having from 1 to 3 carbon atoms.
31. A compound of claim 30 wherein R² is a hydrogen atom.

32. A compound of claim 30 wherein R⁷ is oxo.
33. A compound of claim 32 wherein each of R¹⁰ and R" is a hydrogen atom.
34. A compound of claim 28 wherein each of R² and R³ is a hydrogen atom.
35. A compound of claim 1 wherein R¹ and R³ are joined so as to form a polymethylene bridge.
36. A compound of claim 1 wherein R³ is phenyl or substituted phenyl.
37. A compound of claim 20 wherein R¹ and R³ are joined so as to form a polymethylene bridge.
38. A compound of claim 20 wherein R³ is phenyl or substituted phenyl.
39. A compound of claim 20 wherein the total number of carbon atoms of R² plus R³ does not exceed 4.
40. A compound of claim 39 wherein R² is a hydrogen atom.
41. A compound of claim 39 wherein R³ is alkyl having 3 carbon atoms.
42. A compound of claim 20 wherein each of R² and R³, independently, is a hydrogen atom or alkyl.
43. A pharmaceutical composition comprising a pharmaceutically acceptable carrier and an amount of a compound of the formula:

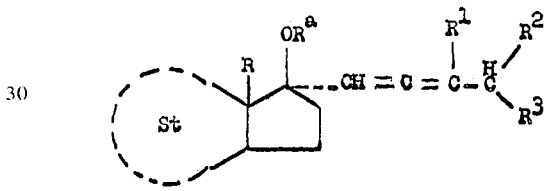

wherein

R is alkyl having from 1 to 4 carbon atoms;
R" is a hydrogen atom, or the residue of a hydrolyzable ether or ester;
R¹ is a hydrogen atom or alkyl having from 1 to 6 carbon atoms;
R² is a hydrogen atom or alkyl having from 1 to 8 carbon atoms;
R³ is a hydrogen atom, alkyl having from 1 to 8 carbon atoms, phenyl, or phenyl having one or two substituents selected, independently, from the group of fluoro or alkyl having from 1 to 6 carbon atoms; or
R¹ and R³ may be joined so as to form a polymethylene bridge having from 3 to 12 carbon atoms; and
St is a gonene residue selected from the group consisting of:

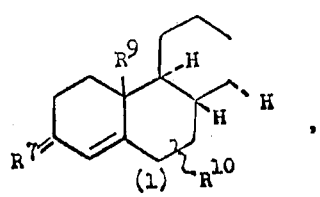

(1)

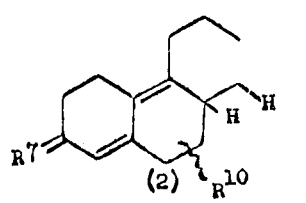

(2)

37

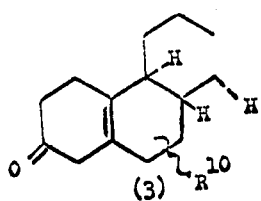

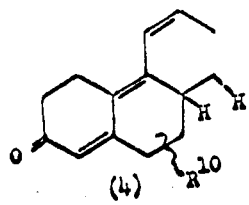

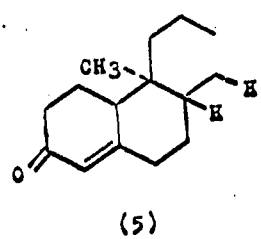

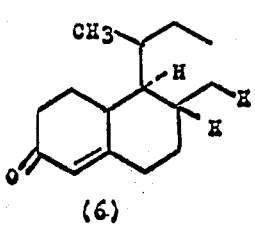

38

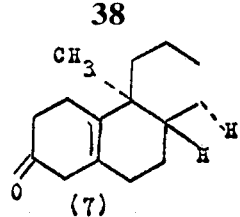

and

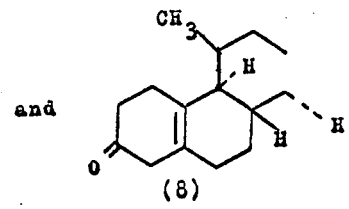

wherein R⁷ is oxo or

or

R⁸ is a hydrogen atom, a hydrolyzable ether or ester residue;
R⁹ is a hydrogen atom or methyl; and
R¹⁰ is a hydrogen atom, 6α-methyl or 7α-methyl; effective in controlling fertility in a warm blodded animal.

44. The method of regulating fertility in a warm blooded animal by parenterally or orally administering to said animal, an amount effective for regulating fertility in said animal of a compund of the formula

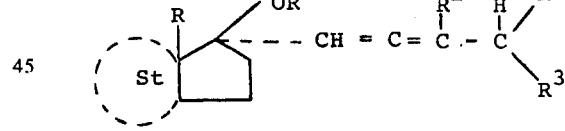

in which R, Rᵃ, R¹, R², R³ and St are as defined in claim 43.

* * * * *